(12) United States Patent
Bradshaw

(10) Patent No.: US 6,450,988 B1
(45) Date of Patent: Sep. 17, 2002

(54) CENTERING CATHETER WITH IMPROVED PERFUSION

(75) Inventor: Anthony J. Bradshaw, Sugar Land, TX (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/474,665

(22) Filed: Dec. 29, 1999

(51) Int. Cl.[7] .............................................. A61M 29/00
(52) U.S. Cl. ............................ 604/96.01; 604/103.08; 600/3
(58) Field of Search ..................... 604/96.01, 101.05, 604/101.01, 103.03, 103.06, 103.07, 103.08, 916; 600/3

(56) References Cited

U.S. PATENT DOCUMENTS

| | | |
|---|---|---|
| 4,762,130 A | 8/1988 | Fogarty et al. |
| 5,019,042 A | 5/1991 | Sahota |
| 5,295,959 A | 3/1994 | Gurbel et al. |
| 5,308,356 A | 5/1994 | Blackshear, Jr. et al. |
| 5,383,856 A | 1/1995 | Bersin |
| 5,395,333 A | 3/1995 | Brill |
| 5,423,745 A * | 6/1995 | Todd et al. ............... 604/53 |
| 5,484,411 A | 1/1996 | Inderbitzen et al. |
| 5,501,667 A | 3/1996 | Verduin, Jr. |
| 5,540,659 A | 7/1996 | Teirstein |
| 5,545,132 A | 8/1996 | Fagan et al. |
| 5,599,306 A | 2/1997 | Klein et al. |
| 5,643,171 A | 7/1997 | Bradshaw et al. |
| 5,653,690 A * | 8/1997 | Booth et al. ............ 604/96 |
| 5,782,740 A | 7/1998 | Schneiderman |
| 5,797,869 A | 8/1998 | Martin et al. |
| 5,797,948 A | 8/1998 | Dunham |
| 5,840,064 A | 11/1998 | Liprie |
| 5,851,171 A | 12/1998 | Gasson |
| 5,882,290 A | 3/1999 | Kume |
| 5,910,101 A | 6/1999 | Andrews et al. |
| 5,938,582 A | 8/1999 | Ciamacco, Jr. et al. |
| 5,947,924 A | 9/1999 | Liprie |
| 5,951,458 A | 9/1999 | Hastings et al. |
| 5,976,106 A | 11/1999 | Verin et al. |
| 6,117,386 A * | 9/2000 | Stiger ..................... 264/526 |
| 6,258,099 B1 * | 7/2001 | Mareiro et al. ............ 606/108 |

FOREIGN PATENT DOCUMENTS

| | | |
|---|---|---|
| DE | 4001086 A1 | 1/1990 |
| WO | WO 94/25106 | 10/1994 |
| WO | WO 95/17223 | 6/1995 |
| WO | WO 96/10436 | 4/1996 |

OTHER PUBLICATIONS

Gebrauchsmuster G 91 02 312.2, 15 pages, together with English Translation and Cover page, 14 pages.

* cited by examiner

Primary Examiner—Michael J. Hayes
(74) Attorney, Agent, or Firm—Blakely, Sokoloff, Taylor & Zafman LLP

(57) ABSTRACT

A centering catheter with engagement knobs to provide improved perfusion in a vessel during intravascular radiation therapy. In one embodiment, a helical centering balloon catheter includes a helical centering balloon formed of helical lobes having a plurality of engagement knobs that outwardly protrude from the helical lobes. The helical lobes form a main spiral perfusion channel for perfusion of blood past the centering catheter. The engagement knobs compliantly engage the vessel walls and offset of the helical lobes such that auxiliary perfusion channels are formed around the engagement knobs between the helical lobes and the walls of the vessel to allow additional perfusion. In the event of a partial obstruction of the spiral channel or a single point failure, the auxiliary perfusion channels allow perfusion past the obstruction.

29 Claims, 3 Drawing Sheets

CENTERING CATHETER WITH IMPROVED PERFUSION

FIELD OF THE INVENTION

The present invention relates to the field of intravascular radiation therapy. In particular, the present invention relates to catheters used for intravascular delivery of radiation.

DESCRIPTION OF RELATED ART

Coronary artery balloon angioplasty is a minimally invasive technique developed as an alternative to coronary artery bypass grafting for treatment of atherosclerosis, the principle process of heart disease. There are about 450,000 coronary interventions, i.e., angioplasty, atherectomy, and stent, performed annually in the U.S. However, a major limitation of this clinical procedure is the high prevalence of restenosis, or re-narrowing, of the treated vessel. Restenosis occurs approximately 30–50% of the time.

Restenosis occurs as result of injury to the vessel wall due to the angioplasty procedure, or to other procedures, i.e., stenting, atherectomy, that compress or remove the atherosclerotic material and may cause trauma to the vessel. Restenosis is a complex process, which can involve an immediate vascular recoil, neointimal hyperplasia, and/or late vascular remodeling. Neointimal hyperplasia, a response of the body to balloon-induced physical injury of the vessel wall, is thought to be the main contributor to restenosis. Hyperplasia can result in narrowing of the vessel lumen within 3–6 months after angioplasty due to proliferation of smooth muscle cells in the region traumatized by the angioplasty. Restenosis can require the patient to undergo repeat angioplasty procedures or by-pass surgery with added costs and risks to the patient.

One method currently used to inhibit restenosis following a procedure such as angioplasty, involves delivery of a prescribed dose of radiation to the walls of the dilated length of vessel through intravascular radiotherapy (IRT). In an example of one method of IRT, a catheter is inserted into a vessel and positioned within the length of vessel dilated by the angioplasty procedure. Once the catheter is positioned, a radiation source is inserted into the lumen of the catheter and positioned to allow delivery of a prescribed dose of radiation to the vessel over a period of time. As a radiation source is relatively small, the radiation therapy may require the radiation source to remain positioned a minimum of four minutes in the vessel. To maintain the position of the catheter within the vessel, some IRT catheters are structured to engage the vessel walls until the radiation therapy is complete.

A consideration in the design of the above IRT catheters is the effect on blood flow in the vessel. If an IRT catheter is structured so that it obstructs blood flow within the vessel over a prolonged period, for example, more than one minute, this may result in impaired heart function, angina, cardiac arrest, or myocardial infarction. Should a low blood flow rate, e.g., a low perfusion flow rate, be detected, the IRT is typically stopped and the catheter withdrawn to allow the blood flow to reestablish and the area to recover. The IRT must then be restarted to complete the therapy session. This can result in a prolonged treatment period and discomfort to the patient.

Alternatively, if an IRT catheter is structured much smaller than the vessel diameter to allow a higher perfusion flow rate, the catheter may not adequately engage the vessel wall and the radiation source may not be centered such that the vessel would receive a non-uniform delivery of the radiation.

For a given radiation source, the intensity of the radiation drops rapidly as a function of distance from the source axis, i.e., a small change in distance from the source to the surface of the vessel wall can result in a large difference in the radiation intensity. Thus, if the radiation source is positioned close to the vessel wall, the wall may receive an overdose of radiation, e.g., a "hot" spot develops. Overdosing a vessel wall with radiation can result in vessel damage, such as inflammation, hemorrhaging, and arterial necrosis. Conversely, the opposite side of the vessel may receive an underdose of radiation that may result in no inhibition of restenosis.

In order to mitigate both the effects of low perfusion flow rates and of overdosing or underdosing a vessel, other catheters, such as centering catheters have developed structures which compliantly engage, or self-fit within, the walls of the vessel to both deliver an approximately uniform dose of radiation and to maintain the catheter position within the vessel. Typically, portions of the catheter structure contact the vessel wall while providing openings for perfusion past the catheter.

U.S. Pat. No. 5,643,171 to Bradshaw et al. describes several embodiments of a centering catheter that may be used with IRT. In one embodiment, a centering balloon is attached to the portion of the catheter in which the radiation source is to be located. The centering balloon can then be inflated until it compliantly engages the vessel wall. In one embodiment, the centering balloon may be formed of helical lobes that substantially center the radiation source within the lumen of the vessel and allow perfusion past the catheter through a main spiral perfusion channel created between the helical lobes of the balloon.

However, it has been noted that single point failures can occur during use of the helical balloon structure, as well as in other structures with a continuous perfusion channel, such as spiral structures. Single point failures occur when an obstruction, such as plaque debris or a blood clot, block perfusion through the main spiral perfusion channel. As the helical structure uses compliant engagement to maintain positioning, portions of the catheter contact the vessel wall and prevent perfusion past the blockage through an alternate path. Thus, the obstruction can cause the perfusion flow rate, even with the helical centering catheter, to stop or to drop to such a low rate that the IRT must be discontinued until the area is recovered.

Thus, what is needed is an apparatus for improving perfusion in centering catheters with helical or spiral shaped base forms in order to mitigate the effects of single point failures.

SUMMARY OF THE INVENTION

The present invention includes a centering catheter for improved perfusion which has a centering segment with lobes which form at least one main perfusion channel, and a plurality of engagement knobs that compliantly engage the walls of the vessel and form auxiliary perfusion channels.

DESCRIPTION OF THE DRAWINGS

The present invention may best be understood by referring to the following description and accompanying drawings which are used to illustrate embodiments of the invention. In the drawings.

DETAILED DESCRIPTION OF THE INVENTION

The present invention includes a centering catheter with engagement knobs to provide improved perfusion in a vessel during intravascular radiation therapy.

Figure 1:
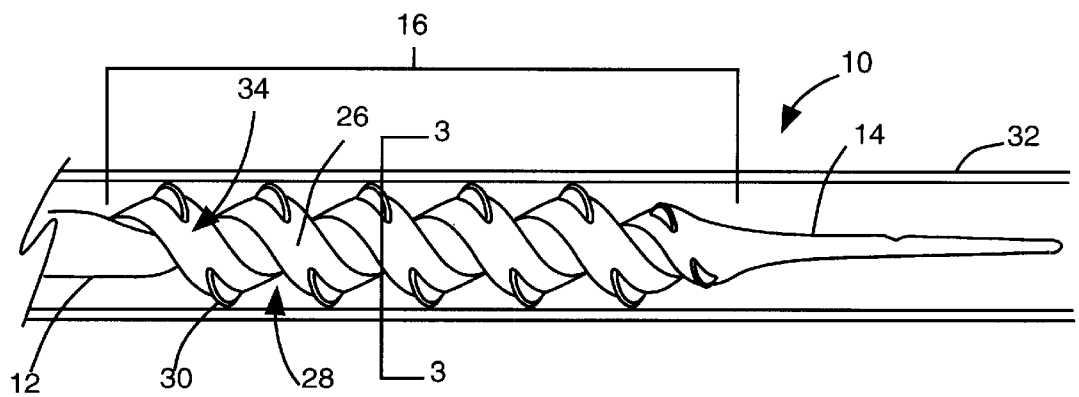
FIG. 1 illustrates one embodiment of the present invention positioned within a vessel.

FIG. 1 illustrates one embodiment of the present invention positioned within a vessel. The embodiment of FIG. 1 includes a helical balloon centering catheter 10 which has a cylindrical shaft 12 having a proximal end and a distal tip 14 and a helical centering balloon 16 located proximal to the distal tip 14. It is to be understood that although the present example is discussed with reference to a helical structure centering catheter, the present invention may be used to improve perfusion of other catheters that utilize compliant engagement within a vessel, for example, straight channeled catheters. In the illustration, the helical balloon centering catheter 10 is shown positioned within a length of vessel 32 that is to receive intravascular radiation therapy (IRT). In one example, the helical centering balloon 16 may be positioned within a length of vessel 32 that has been dilated using an angioplasty procedure and is to receive a prescribed dose of radiation to prevent restenosis of the dilated length.

In one embodiment, the helical centering balloon 16 may be formed as a continuous, inflatable, spiral of helical lobes 26 with a plurality of engagement knobs 30 that externally protrude from the helical lobes 26. In one embodiment, the engagement knobs 30 are formed as an integral part of the balloon lobe shape of the helical lobes 26. As the helical lobes 26 advance and spiral along the length of the helical centering balloon 16, a continuous main spiral perfusion channel 28 is formed between the helical lobes 26 that allow perfusion past the catheter 10. The engagement knobs 30 act to compliantly engage the walls of the vessel 32 when the helical centering balloon 16 is inflated, and maintain the position of the helical balloon centering catheter 10 within the vessel 32 during radiation therapy. Additionally, the engagement knobs 30 offset the helical lobes 26 a small distance away from the wall of the vessel 32 to create auxiliary perfusion channels 34 for increased perfusion past the helical balloon centering catheter 10. In the event that the main spiral perfusion channel 28 becomes partially obstructed or experiences a single point failure, the auxiliary perfusion channels 34 provide alternate paths for perfusion past the obstruction. It is to be noted that in compliantly engaging the vessel walls, the engagement knobs 30 may flatten somewhat, thus the perfusion flow rate through the auxiliary perfusion channels 34 may vary depending upon the fit of the helical centering balloon 16 within the vessel 32. In the present example, the engagement knobs 30 may be formed as hollow, teardrop-shaped outward protrusions of the helical lobes 26. In another example, described further herein with reference to FIGS. 4 and 5, the engagement knobs 30 may also be hemispherical in shape. Other shapes may also be utilized so long as the shape allows for compliant engagement of the vessel wall and formation of auxiliary perfusion channels.

In one embodiment, the engagement knobs 30 may be located along the outer spiral midline of the helical lobes 26 with a spacing of five (5) engagement knobs 30 per revolution. Other numbers of engagement knobs 30 and spacing per revolution may also be used, but a spacing of three to five (3–5) engagement knobs 30 per revolution is preferred. Further, the engagement knobs 30 may be positioned in patterns, other than along the spiral midline, for example, in a random pattern, or in multiple rows.

Figure 2:
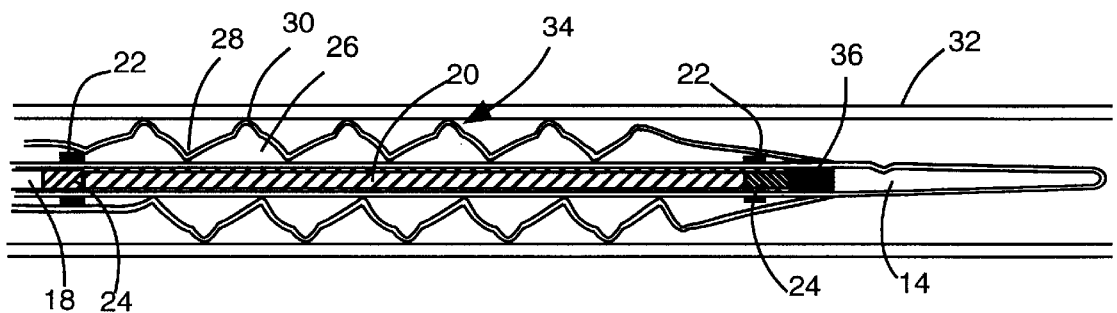
FIG. 2 illustrates a longitudinal cross-sectional view of the embodiment of the present invention shown in FIG. 1.

FIG. 2 illustrates a longitudinal cross-sectional view of the example shown in FIG. 1. The shaft 12 has a lumen 18 for receiving a radiation source 20, for example, a radioactive source wire. Additionally, the shaft 12 may have a balloon inflation lumen (not shown) to allow inflation of the helical centering balloon 16 from a source proximal to helical centering balloon 16, as well as a guidewire lumen for receiving a guidewire (not shown), and a support lumen for receiving a support mandrel (not shown). The balloon inflation lumen, guidewire lumen, and support lumen are structures well known by those of ordinary skill in the art and are not discussed so that the present invention may be more clearly illustrated. It is to be understood that the present invention can be utilized with different guidewire and support systems and that the present example is not meant to be limiting on the invention.

The lumen 18 opens at the proximal end of the shaft 12 and terminates at the distal tip 14. The lumen 18 may be separated from a guidewire lumen by a plug 36. As the helical lobes 26 spiral around the lumen 18, an effective outer diameter is created which substantially centers the lumen 18 within the lumen of the vessel 32. Upon insertion of a radiation source 20 into the lumen 18, the radiation source 20 is then substantially centered within the lumen of the vessel 32 so that an approximately uniform dose of radiation is delivered to the vessel wall.

In the illustration, it can be seen that the engagement knobs 30 are formed as an integral part of the helical lobes 26, and are positioned along the exterior portions of the helical lobes 26 to offset the helical lobes 26 from the walls of the vessel 32. Thus, where prior art centering catheters utilizing compliant engagement may have had the helical lobes compliantly engaging the vessel wall, in the present invention, the engagement knobs 30 compliantly engage the vessel wall and form the auxiliary perfusion channels 34. As the engagement knobs 30 may be located on the exterior portions of the helical lobes 26, the spiraling of the helical lobes 26 with the engagement knobs 30 creates an offset that is substantially the same along the length of the helical centering balloon 16 such that an effective diameter is maintained and the radiation source 20 remains substantially centered within the lumen of the vessel 32. In this way, the auxiliary perfusion channels 34 provide perfusion in addition to that through the main spiral perfusion channel 28 to provide an improved perfusion flow rate. Additionally, should the main spiral perfusion channel 28 become partially obstructed or experience a single point failure, the auxiliary perfusion channels 34 allow perfusion around the blockage. Thus, the likelihood that an IRT session will be disrupted due to a low perfusion flow rate may be reduced.

In one embodiment, the proximal end of the helical balloon centering catheter 10 may be connected to an afterloader or other device for delivery of intravascular radiation. In one example, the helical balloon centering catheter 10 may be connected to an afterloader device utilizing a key connector that allows the afterloader device to identify the particular characteristics of the helical balloon centering catheter 10. The afterloader device may then be used to automatically position the radiation source 20, i.e., a radioactive source wire, within the helical balloon centering catheter 10 to deliver the prescribed radiation therapy to the patient. It is to be understood that the helical balloon centering catheter 10 may be used with hand-loaded radioactive ribbons and wire, or with other radiation delivery devices and that the use of an afterloader device is not a limitation on the present invention.

Radio-opaque markers 22 may be attached to the helical balloon centering catheter 10 to delineate a treatment length determined according to a particular radiotherapy method. The radio-opaque markers 22 may be gold, iridium or other materials commonly used for positioning catheters under fluoroscopy, and are attached by conventional means to the shaft 12. In one example, the radio-opaque markers 22 may delineate the length within the helical centering balloon 16 over which the radiation source 20 will deliver a radiation dose. Although the present illustration shows a single radiation source 20 of one length with source end markers 24, it is to be understood that a smaller radiation source may be utilized according to a stepping protocol where the smaller radiation source is advanced along the lumen 18 until a prescribed dose of radiation is delivered to the treatment length.

In the present example, the helical centering balloon 16 with the engagement knobs 30 may be fabricated using standard techniques well known by those of ordinary skill in the art. In one example, the helical centering balloon 16 may be fabricated using a shape mold and materials of relatively high strength that will expand to a fixed diameter when inflated, such as relatively high strength polymers, i.e., nylon, polyester, or polyvinyl acetate or polyethylene. The helical centering balloon 16 may be attached to the shaft 12 by bonds that are located at the ends, at regular intervals, or are continuous over the length of the helical centering balloon 16. The bonds may be thermal or ultrasonic welds, adhesive or solvent bonds, or other conventional means.

Figure 3A:
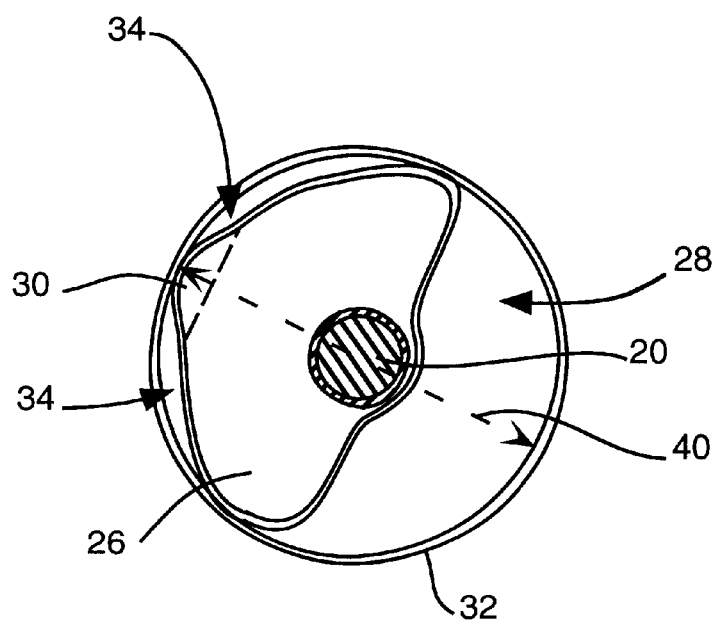
FIG. 3A illustrates a transverse sectional view of the embodiment of the present invention shown in FIG. 1 taken along line 3—3.

FIG. 3A illustrates a transverse sectional view of the embodiment of the present invention shown in FIG. 1 taken along line 3—3. In this example, the radiation source 20 within the lumen 18 is substantially centered within the vessel 32 due to the effective diameter 40 created by the protrusions of the engagement knobs 30 from the helical lobes 26 as the helical lobes 26 spiral. This allows for a uniform dose of radiation to be delivered to the vessel wall along the treatment length. In this example, the engagement knobs 30 are shown as a hollow, teardrop shapes and form auxiliary perfusion channels 34 to allow additional perfusion past the helical centering balloon catheter 10. When the helical centering balloon 16 is properly inflated, the engagement knobs 30 may outwardly protrude a distance 42 of approximately 0.25 mm to 0.75 mm, depending upon the diameter of the helical centering balloon 16. It is to be noted that although the teardrop shape is shown so that the teardrops taper in a direction parallel with the spiral of the helical lobes 26, the teardrop shape may also be perpendicular to the spiral, or at another angle to the spiral. Further, although not shown, as earlier discussed, additional lumens for guidewires and/or support wires may also be incorporated into the helical centering balloon 16 utilizing standard techniques well-known by those of ordinary skill in the art. It is to be understood that although the engagement knobs 30 are formed as hollow protrusions in the present examples, they may be formed by other methods and in other shapes, so long as the engagement knobs 30 can compliantly engage the walls of a vessel and allow the formation of auxiliary channels.

Figure 3B:
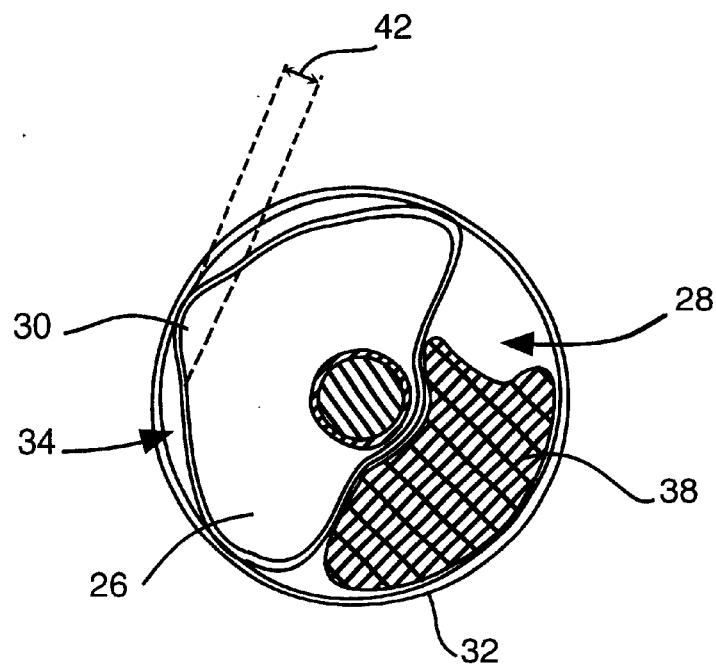
FIG. 3B illustrates a transverse sectional view of the embodiment of the present invention shown in FIG. 3A with a blockage of the main perfusion channel.

FIG. 3B illustrates a transverse sectional view of the embodiment of the present invention shown in FIG. 3A with a blockage 38 of the main perfusion channel 28. Without the engagement knobs 30, the perfusion flow rate may be negatively impacted by the blockage 38 resulting in a decreased flow rate or single point failure. As earlier described, either of these situations may result in the IRT procedure being terminated until blood flow is reestablished in the vessel. However, the presence of the engagement knobs 30, provide the auxiliary channels 34 through which perfusion can continue past the blockage 38. This allows perfusion to reestablish past the blockage 38 in the main perfusion channel 28, as well as in the auxiliary channels 34. The improved perfusion may allow the IRT procedure, that may have been terminated utilizing prior art centering catheters, to continue to completion despite the blockage 38.

Figure 4:
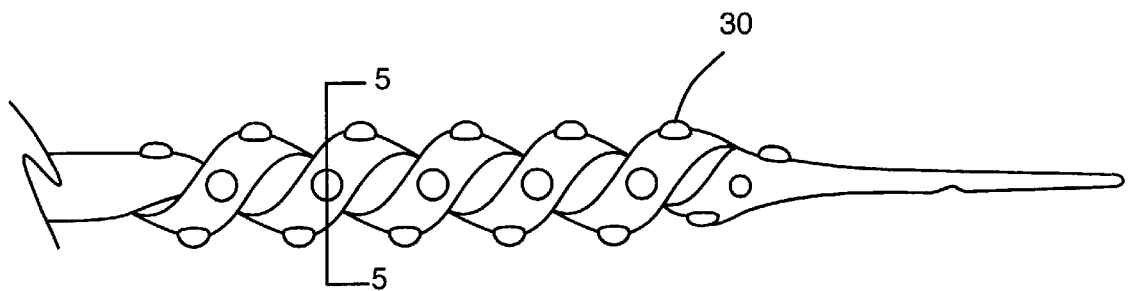
FIG. 4 illustrates another embodiment of the present invention.

FIG. 4 illustrates another embodiment of the present invention. In this example, the helical lobes 26 have engagement knobs 30 that are hemispherical in shape rather than teardrop-shaped as described in the first example. In one embodiment, the engagement knobs 30 may be located along the outer spiral midline of the helical lobes 26 with a spacing of five (5) engagement knobs 30 per revolution. Other numbers of engagement knobs 30 and spacing per revolution may also be used, but a spacing of three to five (3–5) engagement knobs 30 per revolution is preferred. Further, the engagement knobs 30 may be positioned in patterns, other than along the outer spiral midline, for example, in a random pattern, or in multiple rows.

Figure 5:
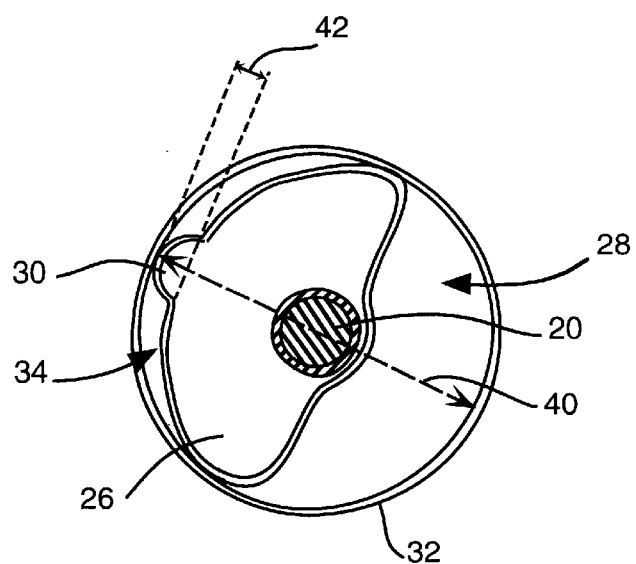
FIG. 5 illustrates a transverse sectional view of the embodiment of the present invention shown in FIG. 4 taken along the line 5—5.

FIG. 5 illustrates a transverse sectional view of the embodiment of the present invention shown in FIG. 4 taken along the line 5—5. In this embodiment, the radiation source 20 within the lumen 18 is substantially centered within the vessel 32 due to the effective diameter 40 created by the protrusions of the engagement knobs 30 from the helical lobes 26 as the helical lobes 26 spiral. This allows for a uniform dose of radiation to be delivered to the vessel wall along the treatment length. In this example, the engagement knobs 30 are shown as a hollow, hemispherical shapes and form auxiliary perfusion channels 34 to allow additional perfusion past the helical centering balloon catheter 10. When the helical centering balloon 16 is properly inflated, the engagement knobs 30 may outwardly protrude a distance 42 of approximately 0.25 mm to 0.75 mm, depending upon the diameter of the helical centering balloon 16. Further, although not shown, as earlier discussed, additional lumens for guidewires and/or support wires may also be incorporated into the helical centering balloon 16 utilizing standard techniques well-known by those of ordinary skill in the art. It is to be understood that although the engagement knobs 30 are formed as hollow protrusions in the present example, they may be formed by other methods and in other shapes, so long as the engagement knobs 30 can compliantly engage the walls of a vessel and allow the formation of auxiliary channels.

Thus, the present invention includes a centering catheter with improved perfusion for delivery of intravascular radiation therapy. In one example, the present invention provides a helical balloon centering catheter with engagement knobs that compliantly engage a vessel wall and form auxiliary perfusion channels. The auxiliary perfusion channels provide for perfusion in addition to the perfusion through the main spiral channel formed between the helical lobes. Additionally, should the main spiral channel become partially obstructed or experience a single point failure, the auxiliary perfusion channels provide perfusion paths past the obstruction.

In the foregoing specification, the present invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

I claim:

1. A catheter for improved perfusion when positioned within a vessel, said catheter comprising:
    a segment having lobes which form at least one main perfusion channel, said lobes having a plurality of engagement knobs formed for compliantly engaging the walls of a vessel and forming auxiliary perfusion channels.

2. The catheter of claim 1 wherein said segment is a helical balloon and said lobes are helical lobes.

3. The catheter of claim 2 wherein said engagement knobs are teardrop-shaped, hollow, protrusions from said helical lobes.

4. The catheter of claim 2 wherein said engagement knobs are hemispherical-shaped, hollow, protrusions from said helical lobes.

5. The catheter of claim 1, wherein each of said auxiliary channels is smaller cross-section relative to said at least one main perfusion channel.

6. The catheter of claim 1, wherein said plurality of engagement knobs center said segment within said vessel.

7. A catheter for delivery of intravascular radiation therapy within a vessel comprising:
    a flexible, elongate shaft, said shaft having a lumen for receiving a radiation source; and
    a segment attached to said shaft, said segment comprising helical lobes which form at least one main spiral perfusion channel, said helical lobes having a plurality of engagement knobs outwardly protruding from said helical lobes for compliantly engaging the walls of said vessel and for forming auxiliary perfusion channels to allow increased perfusion past said catheter.

8. The catheter of claim 7 wherein said segment is an inflatable, helical balloon.

9. The catheter of claim 8 wherein said plurality of engagement knobs are teardrop-shaped, outward, hollow protrusions from said helical lobes.

10. The catheter of claim 8 wherein said plurality of engagement knobs is hemispherical-shaped, outward, hollow protrusions from said helical lobes.

11. The catheter of claim 7, wherein said plurality of engagement knobs center said radiation source, within said vessel.

12. The catheter of claim 7, wherein each of said auxiliary channels is smaller cross-section relative to said at least one spiral perfusion channel.

13. A catheter for delivery of intravascular radiation therapy within a vessel, comprising:
    a flexible, elongate shaft, said shaft having a proximal end and distal tip, and a central lumen for receiving a radiation source; and
    an inflatable, helical balloon attached to said shaft and located proximal to said distal tip, wherein said inflatable, helical balloon comprises helical lobes which form at least one main spiral perfusion channel, said helical lobes having a plurality of engagement knobs for compliantly engaging the walls of said vessel and for forming auxiliary perfusion channels to allow increased perfusion.

14. The catheter of claim 13 wherein said plurality of engagement knobs is inflatable, outward, hollow protrusions formed integrally from said helical lobes.

15. The catheter of claim 14 wherein when said helical balloon is properly inflated said plurality of engagement knobs outwardly protrude from said helical lobes a distance in the range of 0.25 mm to 0.75 mm.

16. The catheter of claim 14 wherein said plurality of engagement knobs is teardrop-shaped.

17. The catheter of claim 16 wherein said plurality of engagement knobs are spaced within the range of three to five engagement knobs per revolution.

18. The catheter of claim 14 wherein said plurality of engagement knobs is hemispherical-shaped.

19. The catheter of claim 18 wherein said plurality of engagement knobs are spaced within the range of three to five engagement knobs per revolution.

20. The catheter of claim 13, wherein said plurality of engagement knobs center said radiation source, within said vessel.

21. The catheter of claim 13, wherein each of said auxiliary channels is smaller relative to said at least one spiral perfusion channel.

22. An apparatus, comprising:
    means for compliantly engaging a wall of a vessel; and
    means for forming auxiliary perfusion channels.

23. The apparatus of claim 22 wherein said means for compliantly engaging is a plurality of engagement knobs.

24. The apparatus of claim 23 wherein said plurality of engagement knobs is teardrop-shaped.

25. The apparatus of claim 23 wherein said plurality of engagement knobs are hemispherical-shaped.

26. A catheter, comprising:
    a balloon having a plurality of engagement knobs to engage a vessel wall, wherein each of said plurality of engagement knobs is disposed substantially in an axial direction along said balloon with respect to each other, and wherein said plurality of engagement knobs form a plurality of perfusion channels.

27. The catheter of claim 26, further comprising:
    a central lumen for receiving a radiation source, wherein said plurality of engagement knobs center said radiation source, when present, within said vessel wall, and wherein said plurality of engagement knobs are disposed substantially in a direction that is perpendicular to said axial direction.

28. The catheter of claim 26, wherein said balloon comprises a helically-shaped balloon that forms a spiral perfusion channel.

29. The catheter of claim 26, wherein each of said plurality of engagement knobs is inflatable, outward, hollow protrusions formed integrally from said balloon, and wherein said axial direction is an axis between a proximal and distal end of said balloon.

* * * * *